(12) United States Patent
Azhir

(10) Patent No.: US 12,029,734 B2
(45) Date of Patent: *Jul. 9, 2024

(54) COMPOSITIONS AND METHODS FOR TREATMENT OF SYMPTOMS IN PARKINSON'S DISEASE PATIENTS

(71) Applicant: Tyler Medical Research, LLC, Tyler, TX (US)

(72) Inventor: Arasteh Ari Azhir, Los Altos, CA (US)

(73) Assignee: Tyler Medical Research, LLC, Tyler, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/971,025

(22) Filed: Oct. 21, 2022

(65) Prior Publication Data

US 2023/0414600 A1      Dec. 28, 2023

Related U.S. Application Data

(63) Continuation of application No. 17/694,535, filed on Mar. 14, 2022, now abandoned, which is a continuation of application No. 16/847,282, filed on Apr. 13, 2020, now abandoned, which is a continuation of application No. 15/659,383, filed on Jul. 25, 2017, now Pat. No. 10,653,686, which is a continuation of application No. 14/838,208, filed on Aug. 27, 2015, now abandoned, which is a continuation of application No. 13/541,333, filed on Jul. 3, 2012, now abandoned.

(60) Provisional application No. 61/504,974, filed on Jul. 6, 2011.

(51) Int. Cl.
*A61K 31/465*     (2006.01)
*A61K 9/20*       (2006.01)
*A61K 9/48*       (2006.01)
*A61K 31/198*     (2006.01)

(52) U.S. Cl.
CPC .............. *A61K 31/465* (2013.01); *A61K 9/20* (2013.01); *A61K 9/2004* (2013.01); *A61K 9/2009* (2013.01); *A61K 9/2031* (2013.01); *A61K 9/2054* (2013.01); *A61K 9/2068* (2013.01); *A61K 9/48* (2013.01); *A61K 9/4891* (2013.01); *A61K 31/198* (2013.01)

(58) Field of Classification Search
CPC ...... A61K 9/20; A61K 9/2004; A61K 9/2009; A61K 9/2031; A61K 9/2054; A61K 9/2068; A61K 9/48; A61K 9/4891; A61K 31/465; A61K 31/198
See application file for complete search history.

(56) References Cited

U.S. PATENT DOCUMENTS

| | | | | |
|---|---|---|---|---|
| 10,143,687 B2 * | 12/2018 | Azhir | ...................... | A61K 45/06 |
| 10,653,686 B2 * | 5/2020 | Azhir | ................... | A61K 31/465 |
| 2003/0077297 A1 * | 4/2003 | Chen | ...................... | A61K 38/13 |
| | | | | 424/400 |
| 2008/0260825 A1 * | 10/2008 | Quik | ....................... | A61P 25/16 |
| | | | | 514/23 |
| 2011/0268809 A1 * | 11/2011 | Brinkley | ................. | A61P 25/34 |
| | | | | 424/48 |

FOREIGN PATENT DOCUMENTS

GB        2341802        *   3/2000   ............. A61K 31/55

* cited by examiner

*Primary Examiner* — Blessing M Fubara
(74) *Attorney, Agent, or Firm* — NK Patent Law

(57) ABSTRACT

The invention provides dosage forms and methods utilizing nicotine to treat symptoms of a neurologic disorder. In some embodiments, the invention provides compositions for treatment of gait and balance problems associated with Parkinson's Disease.

18 Claims, 5 Drawing Sheets

FIG. 5

| Parameter | Nicotine (N=35) | PBO (N=27) |
|---|---|---|
| PD Duration (years) | 11.2 (4.7) | 11.1 (5.6) |
| Time Since Start of Levodopa (years) | 9.6 (4.7) | 10.2 (5.4) |
| Time Since Onset of LIDS (years) | 5.3 (3.2) | 5.2 (4.5) |
| UPDRS Total (Parts II+III+IV) | 43.5 (14.0) | 38.3 (11.7) |
| UPDRS Part III | 20.0 (8.8) | 16.9 (8.3) |
| UDPRS Part IV | 10.5 (2.8) | 9.9 (2.8) |
| UPDRS Q32+33 | 4.8 (0.9) | 4.6 (0.8) |
| UDysRS Total | 51.7 (5.4) | 48.1 (15.1) |
| UDysRS Part 1B | 20.5 (7.7) | 18.7 (7.3) |
| UDysRS Part 2B | 5.9 (3.9) | 4.5 (4.0) |
| UDysRS Part 3 | 13.5 (5.4) | 12.7 (4.9) |
| UDysRS Part 4 | 7.8 (2.9) | 7.6 (2.4) |
| LF-ADL | 11.8 (3.3) | 10.9 (3.6) |

COMPOSITIONS AND METHODS FOR TREATMENT OF SYMPTOMS IN PARKINSON'S DISEASE PATIENTS

This application is a continuation of U.S. patent application Ser. No. 17/694,535, filed Mar. 14, 2022, which is a continuation of U.S. patent application Ser. No. 16/847,282, filed Apr. 13, 2020, now abandoned, which is a continuation of U.S. patent application Ser. No. 15/659,383, filed Jul. 25, 2017, now U.S. Pat. No. 10,653,686, issued on May 19, 2020, which is a continuation of U.S. patent application Ser. No. 14/838,208, filed Aug. 27, 2015, now abandoned, which is a continuation of U.S. patent application Ser. No. 13/541,333, filed Jul. 3, 2012, now abandoned, which claims priority from U.S. Provisional Application No. 61/504,974, filed Jul. 6, 2011, the entire contents of each of which are hereby incorporated by reference in their entirety.

BACKGROUND OF THE INVENTION

Parkinson's disease (also known as Parkinson disease, Parkinson's, idiopathic parkinsonism, primary parkinsonism, PD, or paralysis agitans) is a degenerative disorder of the central nervous system. It results from the death of dopamine-containing cells in the substantia nigra, a region of the midbrain; the cause of cell-death is unknown. Early in the course of the disease, the most obvious symptoms are movement- and balance-related, including shaking, rigidity, slowness of movement and difficulty with walking and gait. The main motor symptoms are collectively called parkinsonism, or a "parkinsonian syndrome". The pathology of the disease is characterized by the accumulation of a protein called alpha-synuclein into inclusions called Lewy bodies in neurons, and from insufficient formation and activity of dopamine produced in certain neurons of parts of the midbrain.

Modern treatments try to manage the early motor symptoms of the disease, mainly through the use of levodopa and dopamine agonists. As the disease progresses and dopamine neurons continue to be lost, a point eventually arrives at which these drugs become ineffective at treating the symptoms and at the same time produce a complication called dyskinesia, marked by involuntary writhing movements. Therefore, there is a need in the art to treat motor symptoms in subjects with Parkinson's Disease, including symptoms of Parkinson's Disease as well as symptoms indirectly associated with Parkinson's Disease, such as those arising as side effects of treatment.

SUMMARY OF THE INVENTION

In some aspects, the present disclosure provides for a pulsatile or extended release dosage form for once or twice-daily administration, said form comprising a capsule or tablet comprising an effective amount of nicotine for treatment of symptoms of Parkinson's Disease or symptoms associated with dopaminergic treatment of Parkinson's Disease, wherein said capsule or tablet exhibits extended or pulsatile release of said nicotine. In various aspects, said pulsatile release comprises a first and second release peak, wherein said first release peak occurs within about two hours of administration to a patient, and said second release peak occurs between about two and about twelve hours of administration to a patient. In various aspects, said extended release comprises an efficacious plasma concentration of nicotine or a metabolite thereof within one hour from administration for a duration of at least six hours and further wherein said capsule or tablet achieves a peak plasma concentration of nicotine or a metabolite thereof at least two hours after administration.

Dosage forms according to the invention include capsules and tablets. In various embodiments, a capsule comprises a powder comprising nicotine for providing said first release peak upon administration to a patient, and said capsule further comprises beads comprising nicotine for providing said second release peak upon administration to a patient. In various embodiments, the capsule or tablet comprises a water-swellable polymeric matrix. For example, in various embodiments, the dosage form swells with water upon administration to the subject's upper gastrointestinal tract such that the swellable dosage form promotes gastric retention in the stomach.

In various aspects, the present disclosure provides a delayed release dosage form for once or twice-daily administration, said form comprising a liquid filled capsule comprising an effective amount of nicotine for treatment of symptoms of Parkinson's Disease or symptoms associated with dopaminergic treatment of Parkinson's Disease, wherein said capsule comprises a hard gelatin outer surface.

In various aspects, the present disclosure provides a method of treating gait and balance problems in a subject, comprising administering an oral composition comprising nicotine, wherein the gait and balance problems are direct symptoms of Parkinson's Disease.

In some aspects, the present disclosure provides for a delayed release dosage form for once or twice-daily administration, comprising a tablet core comprising an effective amount of nicotine, the tablet core being surrounded by an outer surface, and an enteric coating completely covering the outer surface of the tablet core, the coating comprising an enteric polymer.

In some aspects, the present disclosure provides for a delayed release dosage form for treatment of gait and balance problems in Parkinson's Disease, comprising a tablet core comprising an effective amount of nicotine, the tablet core being surrounded by an outer surface, and an enteric coating completely covering the outer surface of the tablet core, the coating comprising an enteric polymer.

In some embodiments, the enteric coating dispenses the nicotine in a metered fashion when the pH is above about 5.0. The nicotine can be present at less than about 10 mg. The nicotine can be present at about 6 mg. The nicotine can be present at about 3 mg.

In some embodiments, the enteric polymer is selected from the group consisting of: a methacrylic acid/methacrylic acid ester copolymer, a methacrylic acid/acrylic acid ester copolymer, cellulose acetate phthalate, hydroxypropyl methylcellulose pthalate, hydroxypropyl methyl cellulose acetate succinate, cellulose acetate trimellitate, and polyvinyl acetate phthalate. In some embodiments, a gastric retained swellable, sustained-release tablet has a matrix comprising polyethylene oxide and hydroxypropylmethylcellulose.

In some embodiments, the dosage form is capable of being administered so that one or more metabolites of said nicotine achieves a plasma level of about 1 to about 500 ng/ml within four hours of administration.

In other aspects, the present disclosure provides for a method of treating gait and balance problems in a subject, comprising administering an oral composition comprising nicotine, wherein the gait and balance problems are direct symptoms of Parkinson's Disease.

In some embodiments, the oral composition comprises an enteric coating. In some embodiments, the enteric coating dispenses the nicotine in a metered fashion when the pH is above about 5.0. The nicotine can be present at less than about 10 mg. The nicotine can be present at about 6 mg. The nicotine can be present at about 3 mg. In some embodiments, the enteric polymer is selected from the group consisting of: a methacrylic acid/methacrylic acid ester copolymer, a methacrylic acid/acrylic acid ester copolymer, cellulose acetate phthalate, hydroxypropyl methylcellulose pthalate, hydroxypropyl methyl cellulose acetate succinate, cellulose acetate trimellitate, and polyvinyl acetate phthalate.

In some embodiments, the dosage form is capable of being administered so that one or more metabolites of said nicotine achieves a plasma level of about 1 to about 500 ng/ml within four hours of administration.

In various embodiments, the dosage form of nicotine further comprises a dopaminergic agent such as levodopa and/or carbidopa. In various embodiments, a dopaminergic agent is excluded. For example, in various embodiments, the dosage form and/or method of treatment does not include levodopa and/or carbidopa.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows baseline demographics of subjects of a phase II clinical trial of nicotine.

DETAILED DESCRIPTION OF THE INVENTION

Figure 1:
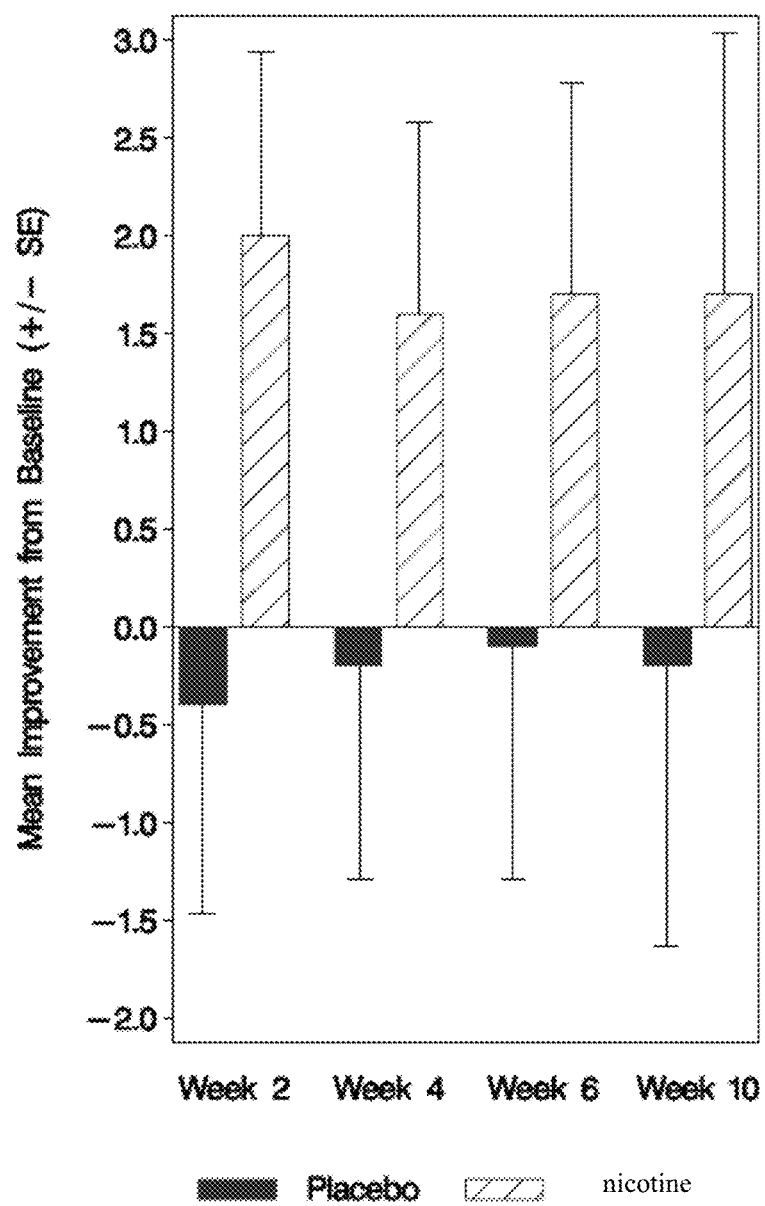
FIG. 1 shows improvement in Unified Parkinson's Disease Rating Scale Part III score for nicotine compared to placebo.

In some aspects, the present disclosure provides for an extended release or pulsatile release dosage form for once or twice-daily administration, said form comprising a capsule or tablet comprising an effective amount of nicotine for treatment of symptoms of Parkinson's Disease or symptoms associated with dopaminergic treatment of Parkinson's Disease, wherein said capsule or tablet exhibits extended or pulsatile release of said nicotine. In various aspects, said pulsatile release comprises a first and second release peak, wherein said first release peak occurs within about two hours of administration to a patient, and said second release peak occurs between about two and about twelve hours of administration to a patient. In various aspects, said extended release capsule or tablet achieves an efficacious plasma concentration of nicotine or a metabolite thereof within one hour from administration for a duration of at least six hours and further wherein said capsule or tablet achieves a peak plasma concentration of nicotine or a metabolite thereof at least about two hours after administration.

Dosage forms according to the invention include capsules and tablets. In various embodiments, said capsule comprises a powder comprising nicotine for providing said first release peak upon administration to a patient, and said capsule further comprises beads comprising nicotine for providing said second release peak upon administration to a patient. Beads are selected from the group consisting of enteric-coated beads, erodible-matrix beads, wax-coated beads, ethylcellulose-coated beads, silicone elastomer coated beads, and combinations thereof. In various embodiments, said capsule comprises a water-swellable matrix to provide a gastroretentive formulation with extended release. A water-swellable matrix may comprise polyethylene oxide, hydroxypropylmethylcellulose, and combinations thereof.

In various embodiments, the dosage form comprises a water-swellable polymeric membrane. Preferably, the water-swellable polymeric membrane ruptures following administration to a patient.

In various embodiments, the dosage form is a tablet. Tablets comprising a coating and a core, wherein said coating comprises nicotine for the first release peak, and said core comprises nicotine for the second release peak, are encompassed. In various embodiments, the coating is selected from an enteric coating, an erodible-matrix coating, a wax coating, an ethylcellulose coating, a silicone elastomer coating, and combinations thereof. In various embodiments, the tablet provides for extended release.

Also disclosed herein is a delayed release dosage form for once or twice-daily administration, said form comprising a liquid filled capsule comprising an effective amount of nicotine for treatment of symptoms of Parkinson's Disease or symptoms associated with dopaminergic treatment of Parkinson's Disease, wherein said capsule comprises a hard gelatin outer surface.

In various embodiments, nicotine is present at less than about 10 mg, or present at about 6 mg, or present at about 4 mg, or present at about 3 mg. In various embodiments, a first pulse of about 1-2 mg nicotine is released in a first release, and a second pulse of about 2-3 mg nicotine is released in a second release.

In various embodiments, the dosage form is capable of being administered so that one or more metabolites of said nicotine achieves a plasma level of about 1 to about 500 ng/ml within four hours of administration.

Also described herein is a method of treating gait and balance problems in a subject, comprising administering an oral composition comprising nicotine, wherein the gait and balance problems are symptoms of Parkinson's Disease. In various embodiments, nicotine is present at less than about 10 mg, or present at about 6 mg, or present at about 4 mg, or present at about 3 mg. In various embodiments, a first pulse of about 1-2 mg nicotine is released in a first release, and a second pulse of about 2-3 mg nicotine is released in a second release. In various embodiments, once-daily administration is provided with an effective serum concentration of nicotine or a metabolite thereof being reached within an hour and being maintained for greater than six hours from administration.

In some embodiments, the present disclosure provides for a delayed release dosage form for once or twice-daily administration, comprising a tablet core comprising an effective amount of nicotine, the tablet core being surrounded by an outer surface, and an enteric coating completely covering the outer surface of the tablet core, the coating comprising an enteric polymer. A delayed release dosage form of the present disclosure may comprise an oral formulation of nicotine.

In other embodiments, the present disclosure provides for a dosage form for treatment of gait and balance problems in Parkinson's Disease (PD), comprising a tablet core comprising an effective amount of nicotine, the tablet core being surrounded by an outer surface, and an enteric coating completely covering the outer surface of the tablet core, the coating comprising an enteric polymer. In various embodiments for direct treatment of symptoms of Parkinson's Disease, a dopaminergic agent may be excluded from the method of treatment. In various embodiments, levodopa and/or carbidopa are excluded from the method of treatment.

In some embodiments, the invention provides compositions and methods utilizing nicotine to reduce, alleviate, or eliminate symptoms of Parkinson's Disease or symptoms associated with Parkinson's Disease, e.g., a side effect associated with dopaminergic agent treatment. In some embodiments, the invention provides compositions and methods utilizing nicotine, e.g., to reduce or eliminate a side effect associated with dopaminergic agent treatment. In some embodiments, the nicotine reduces or eliminates a side effect associated with dopaminergic agent treatment. Dopaminergic agents include a dopamine precursor or a dopamine receptor agonist. Examples of dopaminergic agents include levodopa, bromocriptine, pergolide, pramipexole, cabergoline, ropinorole, apomorphine or a combination thereof.

As used herein, the term "pH independent release" refers to a rate of release of a drug from a dosage form that does not change when the pH of the environment in which the dosage form is found is changed, e.g., from an acidic pH to a higher pH. The term "pH dependent release" refers to a rate of release of a drug from a dosage form that changes when the pH of the environment in which the dosage form is found is changed from, e.g., an acidic pH to a higher pH.

As used herein, the term "zero-order release" refers to a uniform or nearly uniform rate of release of a drug from a dosage form during a given period of release, a rate of release that is independent of the concentration of drug in the dosage form. A dosage form with a zero-order release profile is referred to herein as a "zero-order dosage form." Any zero-order dosage form has the advantage of providing maximum therapeutic value while minimizing side effects.

The term "oral administration," as used herein, refers a form of delivery of a dosage form of a drug to a subject, wherein the dosage form is placed in the mouth of the subject and swallowed.

The term "orally deliverable" herein means suitable for oral administration.

The term "enteric coating," as used herein, refers to a tablet coating that is resistant to gastric juice, and which dissolves after a dosage form with the enteric coating passes out of the stomach, after oral administration to a subject.

A "therapeutic effect," as that term is used herein, encompasses a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. A prophylactic effect includes delaying or eliminating the appearance of a disease or condition, delaying or eliminating the onset of symptoms of a disease or condition, slowing, halting, or reversing the progression of a disease or condition, or any combination thereof.

The term "excipient," as used herein, means any substance, not itself a therapeutic agent, used as a carrier or vehicle for delivery of a therapeutic agent to a subject or added to a pharmaceutical composition to improve its handling, storage, disintegration, dispersion, dissolution, release or organoleptic properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, lubricants, glidants, substances added to mask or counteract a disagreeable taste or odor, flavors, dyes, fragrances, and substances added to improve appearance of the composition.

A pH-dependent delayed release characteristic of one embodiment of the dosage form of the present disclosure result from an enteric coating. Once the dosage form leaves the highly acidic environment of the stomach and enters the higher pH of the lower gastrointestinal tract, the enteric coating dissolves, and the tablet core matrix controls the rate of release of drug remaining therein. The enteric coating preferably dissolves at a pH of at least about 5. In some embodiments, the enteric coating dissolves at a pH of at least about 5.5, 6.0, 6.5, 7.0, 7.5, or 8.0.

In some embodiments, the dosage form comprises an enteric coating and nicotine, wherein the enteric coating dispenses the nicotine in a metered fashion when said pH is above about 5.0. In some embodiments, the dosage form comprises an enteric coating and nicotine, wherein the enteric coating dispenses the nicotine in a metered fashion when said pH is above about 5.5, 6.0, 6.5, 7.0, 7.5, or 8.0.

In some embodiments, in addition to a pH-dependent release rate, the dosage form of the present invention described has a controlled release rate, e.g., a zero-order release rate through changes in pH, such as occur when the dosage form passes from the stomach to the upper intestines of a subject after oral administration thereto. In the case of a human being the average pH of the fluids in a stomach is about pH 1.1, while the average pH of the upper intestinal tract is about pH 5 to about 7.

In some embodiments, an enteric coating is combined with a pore former to effect a pH-independent extended release. A pore former can allow a limited amount of environmental fluids to reach the tablet core in the upper gastrointestinal (GI) tract, including the stomach, thereby permitting a limited amount of drug to be released into the subject at that stage after oral administration. In embodiments containing pore forming agents, the drug in the tablet core diffuses out of the tablet and into the environment surrounding the tablet through channels formed initially through pore forming agents in the enteric coating, and later, after the enteric coating has dissolved, through channels formed in the matrix itself.

In some cases, an enteric coating can be used to reduce the burst effect associated with matrix tablets. This effect is thought to be related to the size of the surface area of a tablet, and to be caused by the amount of drug located on or near the surface of the tablet. This effect can be minimized through the coating of a tablet core matrix with an enteric coating with pore-former distributed therein, as described above. For this embodiment of the invention, the solubility of the drug in the tablet core need be pH dependent. It is contemplated that any drug could be used in this embodiment of the invention, provided its solubility characteristics allow for containment within and release from the matrix. The enteric coating with pore former effectively minimizes the surface area of the tablet that is initially exposed to solution in the GI tract and thus limits the amount of drug that is initially released. The coating composition, in terms of ratio of enteric to pore-former, could be changed to dictate how much the burst is minimized and therefore the release rate of the drug. A pH-sensitive enteric coating dissolves when the tablet enters the intestine and allows the core to take over the control of the tablet release.

The dosage form of the present invention can delay the period of drug release compared to uncoated tablet cores having the same composition as the tablet cores of the present dosage forms. The drug in the coated tablet cores of the present invention delay release of the drug into a subject by at least about 30 minutes, 1 hour, 1.5 hours, 2 hours, 2.5 hours, 3 hours, 4 hours, 5 hours, 6 hours, 7 hours, or 8 hours after oral administration. A dosage form that provides delayed drug release as described herein can be formulated for once or twice-daily administration.

The dosage form of the present invention can extend the period of drug release compared to uncoated tablet cores having the same composition as the tablet cores of the present dosage forms. The drug in the coated tablet cores of the present invention preferably continue to release the drug into a subject to at least 10 hours, more preferably to at least 12 hours, even more preferably to at least 14 hours, and most preferably to at least 16 hours after oral administration. A dosage form that provides continuous drug release over about 10, 11, 12, 13, or 14 hours can be formulated for once or twice-daily administration, thereby allowing continuous delivery of a drug over a 24-hour period.

In various embodiments, the release profile is a pulsatile release. For example, in various embodiments, an immediate release of nicotine is followed by an extended or delayed release of nicotine.

The terms "tablet core," "matrix," and "tablet core matrix" refer to a compressed tablet prior to coating. No specialized geometry of the tablet core is necessary in the present invention. The tablet core may be in any shape known in the pharmaceutical industry and suitable for drug delivery, such as in spherical, cylindrical, or conical shape. In the case of cylindrical shape, it generally has flat, convex, or concave surfaces. The tablet core of the dosage form of the present invention can comprise a matrix of a drug and a water soluble polymer, suitable for sustained or controlled release following exit of the tablet from the acidic environment of the stomach and dissolution of the coating upon entry into the higher pH environment of the intestine.

The tablet core is prepared by conventional dry granulation methods without using a solvent. The enteric coating is applied using a conventional process known in the art. The coated tablets of the present invention have a dual advantage in allowing ease of manufacture and affording medicament release in a substantially linear fashion over an extended period of time.

In some embodiments, the dosage form comprises an enteric coating comprising an enteric polymer. Suitable enteric polymers include, but are not limited to, methacrylic acid/methacrylic acid ester copolymer, a methacrylic acid/acrylic acid ester copolymer, cellulose acetate phthalate, hydroxypropyl methylcellulose pthalate, hydroxypropyl methyl cellulose acetate succinate, cellulose acetate trimellitate, and polyvinyl acetate phthalate.

Enteric polymers suitable for use in the present invention include, but are not limited to polyacrylate copolymers such as methacrylic acid/methacrylic acid ester copolymers or methacrylic acid/acrylic acid ester copolymers, such as USP/NF, Types A, B, or C, which are available from Rohm GmbH under the brand name Eudragit™; cellulose derivatives, such as cellulose acetate phthalate, hydroxypropyl methylcellulose pthalate, hydroxypropyl methyl cellulose acetate succinate, and cellulose acetate trimellitate; and polyvinyl acetate phthalate, such as is available from Colorcon, under the brand name SURETERIC®, and the like. In some embodiments, the enteric polymer is a polyvinyl acetate phtalate.

Suitable water soluble pore-forming agents for use in the enteric coating in the dosage forms of the present invention include, but are not limited to, povidone K 30, polyvinyl alcohol, cellulose derivatives such as hydroxypropyl cellulose, hydroxypropyl methyl cellulose, methyl cellulose or sodium carboxymefhylcellulose; sucrose; xylitol, sorbitol, mannitol, maltose, xylose, glucose, potassium chloride, sodium chloride, polysorbate 80, polyethylene glycol, propylene glycol, sodium citrate, or combinations of any of the above. The pore-forming agent preferably comprises hydroxypropyl methyl cellulose.

The composition of the enteric coating is preferably designed to ensure adherence of the coating to the tablet core. Methods for selection of coating compositions that adhere to compressed tablets are known. See, for example, Pharmaceutical Dosage Forms: Tablets, 2nd ed., vol. 1, Lieberman et al., ed. (Marcel Dekker, Inc.; New York, N.Y.; 1989), pp. 266-271, incorporated herein by reference. Additionally, the cores can be subcoated prior to coating with an enteric coating. The subcoat can function; to provide insure that pores in the core are filled in prior to coating with an enteric coat, (insure against coating failure). The sub coat can consist of any film forming formulation examples include Opadry (Colorcon), Opadry II (Colorcon), AMT (Colorcon) and HPMC.

The enteric coating can be about 3% to about 10% by weight of the dosage form of the present invention. In some cases, the enteric coating can be about 4%, 5%, 6%, 7%, 8%, 9%, 10%, 11%, 12%, 13%, 14%, 15%, 16%, 17%, 18%, 19%, or 20% by weight of the dosage form of the present invention.

In some embodiments, the tablet core of a dosage form of the invention comprises at least one hydrophilic polymer. Suitable hydrophilic polymers include, but are not limited to, hydroxypropyl methylcellulose (hereinafter, "HPMC"), hydroxypropylcellulose, or other water soluble or swellable polymers such as sodium carboxymethyl cellulose, xanthan gum, acacia, tragacanth gum, guar gum, karaya gum, alginates, gelatin, and albumin. The hydrophilic polymers can be present in amounts ranging from about 5% to about 95% by weight of the system. In some embodiments, the hydrophilic polymers are selected from the group consisting of cellulose ethers, such as hydroxypropylmethylcellulose, hydroxypropylcellulose, methylcellulose, and mixtures thereof.

Where a given salt form of a drug is too soluble to provide desired extended release characteristics using a dosage form of the present invention, it may be preferred to use a less soluble form, such as a crystalline form, of the same drug in the dosage form.

The amount of drug in a given dosage form can be selected to accommodate the desired frequency of administration used to achieve a specified daily dosage. The amount of the unit dosage form of the composition that is administered and the dosage regimen for treating the condition or disorder will depend on a variety of factors, including the age, weight, sex and medical condition of the subject, the severity of the condition or disorder, the route and frequency of administration, and the particular drug selected, and thus may vary widely. One or more dosage forms can be administered up to about 6 times a day. In some cases, a dosage form is formulated for once or twice daily administration. However, the dosage forms of the present invention release at a delayed and/or extended rate, making it possible to provide the desired therapeutic efficacy by administration once-a-day or twice-a-day.

Dosage forms of the present invention may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, an agent (e.g., a therapeutic drug or a candidate drug) is formulated as a lyophilizate using appropriate excipient solutions (e.g., sucrose) as diluents. Diluents can be incorporated into the tablet core of a dosage form.

Dosage forms of the invention, preferably the tablet core matrix, optionally comprise one or more pharmaceutically acceptable diluents as excipients. Non-limiting examples of suitable diluents include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of a- and amorphous cellulose (e.g., Rexcel™) and powdered cellulose; calcium carbonate; glycine; bentonite; polyvinylpyrrolidone; and the like. Such diluents, if present, constitute in total about 5% to about 99%. In some embodiments, such diluents constitute in total about 10% to about 85%, or about 10% to about 80%, of the total weight of the composition.

In another embodiment of the invention, the gastric retained dosage form of nicotine is an extended release oral drug dosage form for releasing nicotine into the stomach, duodenum and small intestine of a patient, and comprises: a single or a plurality of solid particles consisting of nicotine or a pharmaceutically acceptable salt thereof dispersed within a polymer that (i) swells unrestrained dimensionally by imbibing water from gastric fluid to increase the size of the particles to promote gastric retention in the stomach of the patient in which the fed mode has been induced; (ii) gradually the nicotine diffuses or the polymer erodes over a time period of hours, where the diffusion or erosion commences upon contact with the gastric fluid; and (iii) releases nicotine to the stomach, duodenum and small intestine of the patient, as a result of the diffusion or polymeric erosion at a rate corresponding to the time period. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in Shell, et al., U.S. Pat. No. 5,972,389 and Shell, et al., WO 9855107, and U.S. Pat. No. 8,192,756, the contents of each of which are incorporated by reference in their entirety.

In yet another embodiment, a bi-layer tablet releases nicotine to the upper gastrointestinal tract from an active containing layer, while the other layer is a swelling or floating layer. Details of this dosage may be found in Franz, et al., U.S. Pat. No. 5,232,704. This dosage form may be surrounded by a band of insoluble material as described by Wong, et al., U.S. Pat. No. 6,120,803.

Another embodiment of the invention uses a gastric retained swellable, sustained-release tablet having a matrix comprised of polyethylene oxide) and hydroxypropylmethylcellulose. Further details may be found in Gusler, et al. "Optimal Polymer Mixtures for Gastric Retentive Tablets," granted as U.S. Pat. No. 6,723,340, the disclosure of which is incorporated herein by reference.

Pharmaceutically acceptable carriers for therapeutic use are well known in the pharmaceutical art, and are described, for example, in Remingtons Pharmaceutical Sciences. Mack Publishing Co. (A. R. Gennaro edit. 1985). For example, sterile saline and phosphate-buffered saline at physiological pH may be used. Preservatives, stabilizers, dyes and other ancillary agents may be provided in the pharmaceutical composition. For example, sodium benzoate, sorbic acid and esters of p-hydroxybenzoic acid may be added as preservatives. In addition, antioxidants and suspending agents may be used. Id. "Pharmaceutically acceptable salt" refers to salts of drug compounds derived from the combination of such compounds and an organic or inorganic acid (acid addition salts) or an organic or inorganic base (base addition salts). The agents, including drugs, contemplated for use herein may be used in either the free base or salt forms, with both forms being considered as being within the scope of the certain present invention embodiments.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, disopropylethylamine, ethanolamine, ethylenediamine, triethanolamine, triethylamine, trisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose, microcrystalline cellulose, and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymefhacrylates; hydroxypropylmethylcellulose; hydroxypropylcellulose (e.g., Klucel™); and ethylcellulose (e.g., Ethocel™). Such binding agents and/or adhesives, if present, can constitute in total about 0.5% to about 25%, about 0.75% to about 15%, or about 1% to about 10%, of the total weight of the composition.

In some embodiments, microcrystalline cellulose is a particularly preferred binder, because of its known chemical compatibility with that particular drug. The use of extragranular microcrystalline cellulose (that is, microcrystalline cellulose added to a wet granulated composition after a drying step) can also be used to improve hardness (for tablets) and/or disintegration time. Microcrystalline cellulose included in dry granulation similarly improves hardness of a tablet core.

Compositions of the invention optionally comprise one or more pharmaceutically acceptable lubricants (including anti-adherents and/or glidants) as excipients. Suitable lubricants include, either individually or in combination, glyceryl behenate (e.g., Compritol™ 888); stearic acid and salts thereof, including magnesium, calcium and sodium stearates; hydrogenated vegetable oils (e.g., Sterolex™); colloidal silica; talc; waxes; boric acid; sodium benzoate; sodium acetate; sodium fumarate; sodium chloride; DLleucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition. In some embodiments, magnesium stearate is a lubricant used to reduce friction between the equipment and granulated mixture during compression of tablet formulations.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or nonionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof. Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkylphenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose monolaurate, sucrose monopalmitate, PEG nonyl phenol series, PEG 15-100 octyl phenol series, and poloxamers. Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Suitable anti-adherents include talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition. Other excipients such as colorants, flavors and sweeteners are known in the pharmaceutical art and can be used in compositions of the present invention.

In some embodiments, the dosage form of the present disclosure comprises: a tablet core comprising nicotine bitartrate dehydrate, magnesium stearate, and microcrystalline cellulose. In some embodiments, the dosage form comprises: a tablet core comprising nicotine in a water soluble polymer matrix; and an enteric coating comprising an enteric polymer and, optionally, a pore-former; wherein, the tablet core or the enteric coating or both include at least one excipient. The dosage form comprises at least one excipient preferably selected from the group consisting of pharmaceutically acceptable diluents, binding agents and lubricants. In some cases, a dosage form comprises at least one excipient selected from the group consisting of lactose (e.g., lactose monohydrate), polyvinylpyrrolidone, magnesium stearate and microcrystalline cellulose.

Standard methods of production are suitably used to produce the dosage forms of the present invention. Dry mixing of intragranular ingredients, followed by granulation, and dry mixing of intragranular ingredients with extragranular ingredients are standard techniques used in the industry. See, for example, Chapter 4 ("Compressed Tablets by Direct Compression," by Ralph F. Shangraw) of Pharmaceutical Dosage Forms: Tablets, vol. 1, 2 ed., Lieberman et al. ed., Marcel Dekker, Inc. pub. (1989), pp. 195-246. The enteric coating is suitably applied using any standard coating technique, such as the techniques described in Chapter 5 ("Compression-Coated and Layer Tablets", by William C. Gunsel et al.), of the same volume.

The present invention is also directed to a method of making the dosage forms of the present invention. In the preferred method, each of the intragranular ingredients is preferably screened or provided in pre-screened form before being dry mixed. If the intragranular ingredients have flow characteristics that make it impracticable to feed the ingredients directly into a tablet press, the ingredients can be granulated prior to compression, for example, by being run through a roller compactor to achieve a suitable ribbon.

When microcrystalline cellulose is included as an excipient in the tablet core, it is preferably included as both an intragranular and as an extragranular ingredient, and added to the other intragranular and extragranular ingredients after each set of ingredients has been mixed, separately. The microcrystalline cellulose is preferably provided pre-screened for particle size prior to addition to the other ingredients. Microcrystalline Cellulose NF Med Powder is an example of one such suitable pre-screened microcrystalline cellulose powder suitable for use in the tablet cores of the present invention.

Once the intragranular ingredients are mixed with all the extragranular ingredients, a compressed tablet is produced therefrom, using any suitable tablet press. Any standard tablet press that does not compress the tablet so far as to damage the water soluble matrix or so compress the tablet that water cannot enter the matrix and solubilize the drug contained therein. The compressed tablets are then completely coated with the enteric coating, comprising an enteric polymer and a pore-former, using any standard coating technique. The enteric coating can be applied in the form of a thin layer.

In some embodiments, the invention includes a multilayer tablet comprising an immediate release layer and a sustained release layer. In some embodiments, the immediate release layer comprises nicotine or a metabolite. In some embodiments, the sustained release layer comprises nicotine or a metabolite. In some embodiments, the immediate release layer and sustained release layer both comprise nicotine or a metabolite.

Nicotine

Nicotine may be isolated and purified from nature or synthetically produced in any manner. This term "nicotine"

is also intended to encompass the commonly occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts. Nicotine is a colorless to pale yellow, strongly alkaline, oily, volatile, hygroscopic liquid having a molecular weight of 162.23. The systematic name of nicotine is 3-[(2S)-1-methylpyrrolidin-2-yl]pyridine and its structure is:

Unless specifically indicated otherwise, the term "nicotine" further includes any pharmacologically acceptable derivative or metabolite of nicotine which exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof. A number of useful derivatives of nicotine are disclosed within the Physician's Desk Reference (most recent edition) as well as Harrison's Principles of Internal Medicine. Methods for production of nicotine derivatives and analogues are well known in the art. See, e.g., U.S. Pat. Nos. 4,590,278; 4,321,387; 4,452,984; 4,442,292; and 4,332,945.

The compounds of the present invention may have asymmetric carbon atoms. All isomers, including diastereomeric mixtures such as racemic mixtures and pure enantiomers are considered as part of the invention.

Without being limited to any one theory, one mechanism of action can be that after a prolong exposure to nicotinic receptor agonist nicotinic receptors become desensitized and the nicotinic receptor agonists start working as nicotinic receptor antagonists. In some embodiments, the nicotinic receptor agonists work as antagonists to reduce or eliminate a side effect induced by a dopaminergic agent.

In some embodiments, the invention provides a composition for administration of nicotine to an animal. In some embodiments, the invention provides a composition for administration of nicotine to an animal to reduce a side effect of a dopaminergic agent, e.g., for the oral delivery of nicotine, that contain at least about 1, 5, 10, 20, 30, 40, 50, 60, 70, 80, 90, 95, 99, 99.5, 99.9, or 99.99% nicotine. In some embodiments, the invention provides a composition for the oral delivery of nicotine that contains no more than about 2, 5, 10, 20, 30, 40, 50, 60, 70, 80, 90, 95, 99, 99.5, 99.9, 99.99, or 100% nicotine. In some embodiments, the invention provides a composition that contains about 1-100% nicotine, or about 10-100% nicotine, or about 20-100% nicotine, or about 50-100% nicotine, or about 80%-100% nicotine, or about 90-100% nicotine, or about 95-100% nicotine, or about 99-100% nicotine. In some embodiments, the invention provides a composition that contains about 1-90% nicotine, or about 10-90% nicotine, or about 20-90% nicotine, or about 50-90% nicotine, or about 80-90% nicotine. In some embodiments, the invention provides a composition that contains about 1-75% nicotine, or about 10-75% nicotine, or about nicotine, or about 50-75% nicotine. In some embodiments, the invention provides a composition that contains about 1-50% nicotine, or about 10-50% nicotine, or about 20-50% nicotine, or about 30-50% nicotine, or about 40-50% nicotine. In some embodiments, the invention provides a composition that contains about 1-40% nicotine, or about 10-40% nicotine, or about 20-40% nicotine, or about 30-40% nicotine. In some embodiments, the invention provides a composition that contains about 1-30% nicotine, or about 10-30% nicotine, or about 20-30% nicotine. In some embodiments, the invention provides a composition that contains about 1-20% nicotine, or about 10-20% nicotine. In some embodiments, the invention provides a composition that contains about 1-10% nicotine. In some embodiments, the invention provides a composition that contains about 1, 2, 5, 10, 20, 30, 40, 50, 60, 70, 80, 90, 95, 96, 97, 98, or 99% nicotine.

In some embodiments, the a concentration of nicotine is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.01%, 0.009%, 0.008%, 0.007%, 0.006%, 0.005%, 0.004%, 0.003%, 0.002%, 0.001%, 0.0009%, 0.0007%, 0.0006%, 0.0005%, 0.0004%, 0.0003%, 0.0002%, or 0.0001% w/w, w/v or v/v.

In some embodiments, a concentration of nicotine is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25% 12%, 11.75%, 11.50%, 11.25% 11%, 10.50%, 10.25% 10%, 9.75%, 9.50%, 9.25%, 9%, 8.75%, 8.50%, 8.25% 8%, 7.75%, 7.50%, 7.25% 7%, 6.75%, 6.50%, 6.25% 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.08%, 0.07%, 0.06%, 0.05%, 0.04%, 0.03%, 0.02%, 0.01%, 0.009%, 0.008%, 0.007%, 0.006%, 0.004%, 0.003%, 0.002%, 0.001%, 0.0009%, 0.0008%, 0.0007%, 0.0006%, 0.0005%, 0.0004%, 0.0002%, or 0.0001% w/w, w/v, or v/v.

In some embodiments, a concentration of nicotine is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately to approximately 14%, approximately 0.9% to approximately 12%, approximately 1% to approximately 10% w/w, w/v or v/v.

In some embodiments, a concentration of nicotine is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately to approximately 2%, approximately 0.08% to approximately 1.5%, approximately 0.09% to approximately 1%, approximately 0.1% to approximately 0.9% w/w, w/v or v/v.

In some embodiments, the amount of nicotine is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, g, 0.0002 g, or 0.0001 g.

In some embodiments, the amount of nicotine is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Nicotinic Receptor Modulators

In one aspect, the invention provides compositions and methods utilizing a nicotinic receptor modulator, e.g., to reduce or eliminate a side effect associated with dopaminergic agent treatment. A nicotinic receptor modulator can be an agonist or it can be an antagonist.

The term "agonist" as used herein refers to a molecule having the ability to initiate or enhance a biological function of a target polypeptide. Accordingly, the term "agonist" is defined in the context of the biological role of the target polypeptide. While preferred agonists herein specifically interact with (e.g. bind to) the target, molecules that enhance a biological activity of the target polypeptide by interacting with other members of the signal transduction pathway of which the target polypeptide is a member are also specifically included within this definition. Agonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

The term "antagonist" as used herein refers to a molecule having the ability to inhibit a biological function of a target polypeptide. Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. Antagonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

In some embodiments, the nicotinic receptor modulator modulates a nicotinic receptor in the brain. In some embodiments, the nicotinic receptor modulator modulates a nicotinic receptor in the striatum or substantia niagra. In some embodiments, the nicotinic receptor modulator modulates a nicotinic receptor comprising at least one a subunit or a nicotinic receptor containing at least one α subunit and at least one β subunit. In some embodiments, the a subunit is selected from the group consisting of α2, α3, α4, α5, α6, α7, α8, α9, and α10 and the β subunit is selected from the group consisting of β2, β3 and β4. In some embodiments, the nicotinic receptor modulator modulates a nicotinic receptor comprising subunits selected from the group consisting of α4β2, α6β2, α4α6β2, α4α5β2, α4α6β2β3, α6β2β3 and α4α2β2. In some embodiments, the nicotinic receptor modulator modulates a nicotinic receptor comprising at least one a subunit selected from the group consisting of α4, α6, and α7.

The nicotinic receptor agonist of the invention may be any ligand that binds to and activates the nicotinic receptor, thereby resulting in a biological response. The potential of a given substance to act as a nicotinic receptor agonist may be determined using standard in vitro binding assays and/or standard in vivo functionality tests.

Other nicotinic receptor agonists include choline esterase inhibitors (e.g., that increase local concentration of acetylcholine), derivatives of epibatidine that specifically bind the neuronal type of nicotinic receptors (with reduced binding to the muscarinic receptor) and having reduced deleterious side-effects (e.g., Epidoxidine, ABT-154, ABT418, ABT-594; Abbott Laboratories (Damaj et al. (1998) J. Pharmacol Exp. Then 284:1058 65, describing several analogs of epibatidine of equal potency but with high specificity to the neuronal type of nicotinic receptors). Further nicotinic receptor agonists of interest include, but are not necessarily limited to, N-methylcarbamyl and N-methylthi-O-carbamyl esters of choline (e.g., trimethylaminoethanol) (Abood et al. (1988) Pharmacol. Biochem. Behav. 30:403 8); acetylcholine (an endogenous ligand for the nicotinic receptor); and the like.

Dopaminergic Agents

In one aspect, the invention provides compositions and methods to reduce or eliminate the effects of a dopaminergic agent. In some embodiments, the compositions and methods retain or enhance a desired effect of the dopaminergic agent, e.g., antiparkinsonian effect. The methods and compositions of the invention apply to any dopaminergic agent for which it is desired to reduce one or more side effects. In some embodiments, the compositions and methods of the invention utilize a dopamine precursor. In some embodiments, the compositions and methods of the invention utilize a dopamine agonist. In some embodiments, the dopaminergic agent is levodopa, bromocriptine, pergolide, pramipexole, cabergoline, ropinorole, apomorphine or a combination thereof. In some embodiments, the dopaminergic agent is levodopa. In some embodiments, the compositions and methods of the invention utilize one or more agents used in the art in combination with a dopamine agent treatment to achieve a therapeutic effect. For instance, in one exemplary embodiment the compositions and methods of the invention utilize levodopa in combination with an agent such as carbidopa, which blocks the conversion of levodopa to dopamine in the blood. In another exemplary embodiment, the compositions and methods of the invention utilize levodopa in combination with a COMT Inhibitor, such as entacapone. In another exemplary embodiment, the compositions and methods of the invention utilize levodopa in combination with a monoamine oxidase type B (MAO-B) inhibitor such as selegiline. In yet another exemplary embodiment, the compositions and methods of the invention utilize levodopa in combination with amantadine.

Levodopa

Levodopa, an aromatic amino acid, is a white, crystalline compound, slightly soluble in water, with a molecular weight of 197.2. It is designated L-3,4-dihydroxyphenylalanine (S)-2-amino-3-(3,4-dihydroxyphenyl)propanoic acid. Its structural formula is

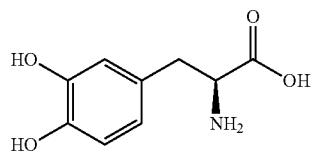 [SMILES: N[C@@H](Cc1ccc(O)c(O)c1)C(=O)O]

Levodopa is used for the treatment of Parkinson's disease. Parkinson's disease is a progressive, neurodegenerative disorder of the extrapyramidal nervous system affecting the mobility and control of the skeletal muscular system. Its characteristic features include resting tremor, rigidity, and bradykinetic movements. Current evidence indicates that symptoms of Parkinson's disease are related to depletion of dopamine in the corpus striatum. Administration of dopamine is ineffective in the treatment of Parkinson's disease apparently because it does not cross the blood-brain barrier. However, levodopa, the metabolic precursor of dopamine, does cross the bloodbrain barrier, and presumably is converted to dopamine in the brain. This is thought to be the mechanism whereby levodopa relieves symptoms of Parkinson's disease.

However, although initially very effective, longterm treatment with levodopa gives rise to multiple complications. Levodopa treatment may cause nausea, vomiting, involuntary movements (e.g. dyskinesias), mental disturbances, depression, syncope, and hallucinations. The precise pathophysiological mechanisms of levodopa side effects are still enigmatic, but are thought to be due to increased brain dopamine following administration of levodopa. Previous work has shown that levodopa induceddyskinesias (LIDs) arise due to enhanced intermittent stimulation of D1, D2 and/or other dopamine receptor subtypes. This results in an imbalance in activity of the two major striatal output pathways, possibly through activation of D1 and inhibition of D2 receptors on the direct and indirect dopaminergic pathways, respectively, although there is some overlap between striatal efferents. Recent data suggest that D1 receptors, through enhanced G-protein coupling, may play a more prominent role in functional hypersensitivity associated with levodopa-induced dyskinesias, while D2 receptor activation may be more closely linked to the antiparkinsonian action of dopaminergic drugs Side Effects The principal adverse reactions of dopaminergic agent include headache, diarrhea, hypertension, nausea, vomiting, involuntary movements (e.g. dyskinesias), mental disturbances, depression, syncope, hallucinations, and abnormal renal function.

The invention provides compositions and methods utilizing nicotine or a nicotinic receptor modulator that reduces or eliminates a side effect associated with dopaminergic agent treatment. In some embodiments, the invention provides compositions and methods utilizing a nicotinic receptor modulator that reduces or eliminates dyskinesias associated with dopaminergic agent treatment. Without being limited to any theory, one possibility is that nicotinic receptor modulator exerts its effect by acting at nicotinic acetylcholine receptors (nAChR), which are expressed in the striatum. There is a dense cholinergic innervation in striatum that closely coincides with dopaminergic neurons. Under physiological conditions, these cholinergic interneurons tonically release acetylcholine, which stimulates nicotinic receptors on dopaminergic nerve terminals to release dopamine. Similarly, exogenously applied agents such as nicotine result in a release of dopamine from striatal terminals.

Methods of Treatment

In some embodiments the invention provides methods of decreasing a side effect of a dopaminergic agent in an animal, e.g. a human, that has received an amount of the dopaminergic agent sufficient to produce a side effect by administering to the animal, e.g., human, an amount of nicotine sufficient to reduce or eliminate the side effect.

The side effect may be acute or chronic. The effect may be biochemical, cellular, at the tissue level, at the organ level, at the multi-organ level, or at the level of the entire organism. The effect may manifest in one or more objective or subjective manners, any of which may be used to measure the effect. If an effect is measured objectively or subjectively (e.g., dyskinesias and the like), any suitable method for evaluation of objective or subjective effect may be used. Examples include visual and numeric scales and the like for evaluation by an individual. A further example includes sleep latency for measurement of drowsiness, or standard tests for measurement of concentration, mentation, memory, and the like. These and other methods of objective and subjective evaluation of side effects by an objective observer, the individual, or both, are well-known in the art.

In some embodiments, the invention provides a composition comprising nicotine, wherein the nicotine is present in an amount sufficient to decrease a side effect of a dopaminergic agent by a measurable amount, compared to the side effect without the nicotine, when the composition is administered to an animal. In some embodiments, a side effect of the dopaminergic agent is decreased by an average of at least about 5, 10, 15, 20, 25, 30, 35, 40, 45, 50, 55, 60, 65, 70, 75, 80, 85, 90, 95, or more than 95%, compared to the side effect without the nicotine. In some embodiments, a side effect of the dopaminergic agent is decreased by an average of at least about 5%, compared to the side effect without the nicotine. In some embodiments, a side effect of the dopaminergic agent is decreased by an average of at least about 10%, compared to the side effect without the nicotine. In some embodiments, a side effect of the dopaminergic agent is decreased by an average of at least about 15%, compared to the side effect without the nicotine. In some embodiments, a side effect of the dopaminergic agent is decreased by an average of at least about 20%, compared to the side effect without the nicotine. In some embodiments, a side effect of the dopaminergic agent is decreased by an average of at least about 30%, compared to the side effect without the nicotine. In some embodiments, a side effect is substantially eliminated compared to the side effect without the nicotine. "Substantially eliminated" as used herein encompasses no measurable or no statistically significant side effect (one or more side effects) of the dopaminergic agent, when a nicotine is administered. In some embodiments, the side effect is dyskinesias.

In some embodiments, the invention provides compositions containing a nicotinic receptor agonist, e.g., nicotine, present in an amount sufficient to decrease a side effect of a dopaminergic agent by an average of at least about 5% and to increase a therapeutic effect of the dopaminergic agent by an average of at least about 5%, when the composition is administered to an animal in combination with the dopaminergic agent, compared to the side effect and therapeutic effect without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 10%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 20% and to increase a therapeutic effect of the dopaminergic agent by an average of at least about 20%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 20%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 30%, when the composition is administered to an animal in combination with the dopaminergic agent, compared to the side effect and therapeutic effect when the dopaminergic agent is administered without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 40%, when the composition is administered to an animal in combination with the dopaminergic agent, compared to the side effect and therapeutic effect when the dopaminergic agent is administered without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 50%, when the composition is administered to an animal in combination with the dopaminergic agent, compared to the side effect and therapeutic effect when the dopaminergic agent is administered without the a nicotinic receptor agonist, e.g., nicotine.

In exemplary embodiments, the invention provides a composition that contains nicotine and a dopaminergic agent, such as levodopa or a dopamine agonist, where the dopaminergic agent is present in an amount sufficient to exert a therapeutic effect, and nicotine is present in an amount effective to decrease a side effect of the dopaminergic agent by a measurable amount (e.g., an average of at least about 5, 10, 15, 20, 30 or more than 30%, as described herein) and to increase the therapeutic effect of the dopaminergic agent by a measurable amount (e.g., an average of at least about 5, 10, 15, 20, 30 or more than 30%, as described herein). The side effect may be any side effect as described herein. In some embodiments, the side effect is dyskinesia.

An "average" as used herein is preferably calculated in a set of normal human subjects, this set being at least about 3 human subjects, preferably at least about 5 human subjects, preferably at least about 10 human subjects, even more preferably at least about 25 human subjects, and most preferably at least about 50 human subjects.

The term "animal" or "animal subject" as used herein includes humans as well as other mammals. The methods generally involve the administration of one or more drugs for the treatment of one or more diseases. Combinations of agents can be used to treat one disease or multiple diseases or to modulate the side-effects of one or more agents in the combination.

The term "treating" and its grammatical equivalents as used herein include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The methods of the invention may be used for treatments of any suitable condition where one or more dopaminergic agents are used that have side effects. Examples of conditions include, but are not limited to, Parkinson's disease, Alzheimer, dopa-responsive dystonia, cerebral palsy, postischemic contractile dysfunction, severe ovarian hyperstimulation syndrome, pediatric movement disorders and non-oliguric renal failure.

In various embodiments, the methods of treatment are directed to direct symptoms of Parkinson's Disease rather than treatment of a dopaminergic agent-induced side effect. For example, in various embodiments, the methods of treatment are directed to treatment of gait and balance deficits resulting directly from Parkinson's Disease. In various embodiments, nicotine is administered separately from any dopaminergic agent. In various embodiments, the subject undergoing treatment with nicotine is not receiving a dopaminergic agent. In various embodiments, the subject undergoing treatment with nicotine is not receiving levodopa, carbidopa, or combinations thereof.

In some embodiments, an effective amount of nicotine is administered such that the nicotine or a metabolite of the nicotine reaches a critical concentration in the bloodstream, plasma, or the tissue. In some embodiments, the nicotine is administered such that the nicotine or a metabolite of nicotine reaches a critical concentration in the bloodstream, plasma or tissue 48, 36, 24, 12, 10, 8, 6, 5, 4, 3, 2, or 1 hours following administration.

In some embodiments, the critical concentration of the nicotine or a nicotine metabolite is about 1 pg/ml to about 1 mg/ml. In some embodiments the critical concentration nicotine or nicotine metabolite is about 1 pg/ml to about 1 ng/ml, or about 50 pg/ml to about 1 ng/ml, or about 100 pg/ml to about 1 ng/ml, or about 500 pg/ml to about 1 ng/ml, or about 1 ng/ml to about 500 ng/ml, or about 10 ng/ml to about 500 ng/ml, or about 100 ng/ml to about 500 ng/ml, or about 200 ng/ml to about 500 ng/ml, or about 300 ng/ml to about 500 ng/ml, or about 400 ng/ml to about 500 ng/ml, or about 500 ng/ml to about 1 ug/ml, or about 600 ng/ml to about 1 ug/ml, or about 700 ng/ml to about 1 ug/ml, or about 800 ng/ml to about 1 ug/ml, or about 900 ng/ml to about 1 ug/ml, or about 1 ug/ml to about 1 mg/ml, or about 10 ug/ml to about 1 mg/ml, or about 100 ug/ml to about 1 mg/ml, or about 500 ug/ml to about 1 mg/ml, or about 600 ug/ml to about 1 mg/ml, or about 700 ug/ml to about 1 mg/ml, or about 800 ug/ml to about 1 mg/ml, or about 900 ug/ml to about 1 mg/ml. In some embodiments, the critical concentration of the nicotine or a nicotine metabolite is about 200 ng/ml to about 420 ng/ml. In some embodiments, the critical concentration of the nicotine or a nicotine metabolite is about 1 ng/ml to about 20 ng/ml. In some embodiments, the critical concentration of the nicotine or a nicotine metabolite is about 1 ng/ml to about 5 ng/ml. In some embodiments, the critical concentration of the nicotine or a nicotine metabolite is about 20 ng/ml to about 100 ng/ml. In some embodiments, the nicotine metabolite is cotinine.

Dosing and Administration

Dosing ranges for dopaminergic agents are known in the art. It is also known in the art that due to intersubject variability in dopaminergic agents, such as levodopa, pharmacokinetics, individualization of dosing regimen is necessary for optimal therapy. For an nicotinic receptor agonist, e.g., nicotine, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of nicotine is about 1, 5, 10, 15, 20, 25, 30, 35, 40, 45, 50, 100, 200, 300, 400, 500, 600, 700, 800, 900, or 1000 mg. In some embodiments, the daily dose of nicotine is 0.9 mg. In some embodiments, the daily dose of nicotine is 1.8 mg. In some embodiments, the daily dose of nicotine is 2.4 mg. In some embodiments, the daily dose of nicotine is 3 mg. In some embodiments, the daily dose of nicotine is 6 mg. In some embodiments, the daily dose of nicotine is 7 mg. In some embodiments, the daily dose of nicotine is 8 mg. In some embodiments, the daily dose is administered in two equal parts during the day, such as about 4 mg twice daily. In some embodiments, the daily dose of nicotine is 9 mg. In some embodiments, the daily dose of nicotine is 12 mg. In some embodiments, the daily dose of nicotine is 14 mg. In some embodiments, the daily dose of nicotine is 18 mg. In some embodiments, the daily dose of nicotine is 21 mg. In some embodiments, the daily dose of nicotine is 24 mg. In some embodiments, the daily dose of nicotine is 32 mg. In some embodiments, the daily dose of nicotine is 50 mg. In some embodiments, the daily dose of nicotine is less than 93 mg.

Daily dose range may depend on the form of nicotinic receptor agonist and/or factors with which the nicotinic receptor agonist is administered, as described herein.

In some embodiment the daily dose of nicotine is such that the plasma level of nicotine or a nicotine metabolite is about 1 pg/ml to about 1 mg/ml. In some embodiments the daily dose of nicotine is such that the plasma level or nicotine or nicotine metabolite is about 1 pg/ml to about 1 ng/ml, or about 50 pg/ml to about 1 ng/ml, or about 100 pg/ml to about 1 ng/ml, or about 500 pg/ml to about 1 ng/ml, or about 1 ng/ml to about 500 ng/ml, or about 10 ng/ml to about 500 ng/ml, or about 100 ng/ml to about 500 ng/ml, or about 200 ng/ml to about 500 ng/ml, or about 300 ng/ml to about 500 ng/ml, or about 400 ng/ml to about 500 ng/ml, or about 500 ng/ml to about 1 ug/ml, or about 600 ng/ml to about 1 ug/ml, or about 700 ng/ml to about 1 ug/ml, or about 800 ng/ml to about 1 ug/ml, or about 900 ng/ml to about 1 ug/ml, or about 1 ug/ml to about 1 mg/ml, or about 10 ug/ml to about 1 mg/ml, or about 100 ug/ml to about 1 mg/ml, or about 500 ug/ml to about 1 mg/ml, or about 600 ug/ml to about 1 mg/ml, or about 700 ug/ml to about 1 mg/ml, or about 800 ug/ml to about 1 mg/ml, or about 900 ug/ml to about 1 mg/ml. In some embodiment, the daily dose of nicotine is such that the plasma level of nicotine or a nicotine metabolite is about 200 ng/ml to about 420 ng/ml. In some embodiment, the daily dose of nicotine is such that the plasma level of nicotine or a nicotine metabolite is about 1 ng/ml to about 20 ng/ml. In some embodiment, the daily dose of nicotine is such that the plasma level of nicotine or a nicotine metabolite is about 1 ng/ml to about 5 ng/ml. In some embodiment, the daily dose of nicotine is such that the plasma level of nicotine or a nicotine metabolite is about 20 ng/ml to about 100 ng/ml.

In some embodiments, nicotine is administered in multiple doses. Dosing may be about once, twice, three times, four times, five times, six times, or more than six times per day. Dosing may be about once a month, once every two weeks, once a week, or once every other day. In some embodiments, dosing is once or twice daily. In some embodiments the administration of nicotine continues for less than about 7 days. In another embodiment the administration continues for more than about 6, 10, 14, 28 days, two months, six months, or one year. In some cases, continuous dosing is achieved and maintained as long as necessary.

Administration of nicotine of the invention may continue as long as necessary. In some embodiments, nicotine of the invention is administered for more than 1, 2, 3, 4, 5, 6, 7, 14, 28 days or 1 year. In some embodiments, nicotine of the invention is administered for less than 28, 14, 7, 6, 5, 4, 3, 2, or 1 day. In some embodiments, nicotine of the invention is administered chronically on an ongoing basis, e.g., for the treatment of chronic effects.

In some embodiments, nicotine is orally administered using an orally disintegrating tablet. Examples of orally disintegrating tablets are known, such as disclosed in U.S. Pat. Nos. 7,282,217; 7,229,641; 6,368,625; 6,365,182; 6,221,392; and 6,024,981.

In various embodiments, nicotine is administered to yield an extended release which comprises a single peak plasma concentration of nicotine or a metabolite thereof, wherein said single peak plasma concentration occurs between about two hours and about 12 hours after administration. In various embodiments, the extended release comprises a single peak plasma concentration of nicotine or a metabolite thereof, wherein said single peak plasma concentration occurs between about six hours and about eight hours after administration. In various embodiments, the extended release achieves an efficacious plasma concentration of nicotine or a metabolite thereof within one hour from administration and achieves a duration of an efficacious plasma concentration of nicotine or a metabolite thereof for a period between about six to about 18 hours from administration. In various embodiments, the extended release achieves an efficacious plasma concentration of nicotine or a metabolite thereof within one hour from administration and achieves a duration of an efficacious plasma concentration of nicotine or a metabolite thereof for a period between about eight hours to about 14 hours from administration. In various embodiments, the extended release achieves an efficacious plasma concentration of nicotine or a metabolite thereof within one hour from administration and achieves a duration of an efficacious plasma concentration of nicotine or a metabolite thereof for a period between about ten hours to about 12 hours from administration.

Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

EXAMPLES

Example 1: Clinical Trial

A total of 65 patients with idiopathic PD and LIDS were enrolled in a phase II study. Major entry criteria were as follows: 1) Hoehn and Yahr Stage II-IV while in "on" state, 2) had moderately to severely disabling LIDS>25% of waking day as determined by a rating of >2 on each of Questions 32 and 33 of the Unified Parkinson's Disease Rating Scale (UPDRS), 3) be on stable doses of levodopa and other medicines for PD for >30 days, 4) have a negative screening urine test for cotinine, and 5) not be a smoker or previous smoker or regular exposure to second-hand smoke. The study consisted of 3 phases: a treatment period of 10 weeks, a 9-day drug taper period, and a 5-day follow-up period. Subjects were randomly assigned to receive either nicotine or placebo (pbo). Dosing began at 1 mg q6 hr and was escalated at 2-week intervals to 6 mg q6 hr (24 mg/day). All subjects were allowed to take ondansetron as rescue medication for the treatment of nausea and/or vomiting for the first 3 days of each dose escalation. Subjects were maintained on 24 mg/day for 4 weeks.

Safety was assessed by incidences of adverse experiences (AE), clinical laboratory tests, serum cotinine, ECG and vital signs. Impulsive symptoms were assessed using the Jay Modified Minnesota Impulsive Disorders Interview (JayMidi). Withdrawal symptoms were evaluated using the Minnesota Nicotine Withdrawal Scale (MNWS-R).

Efficacy was assessed using the UPDRS (total of Parts II+III+IV), sum of Q32+Q33, Unified Dyskiensia Rating Scale (UDysRS) total scores and subscores, Lang-Fahn Dyskinesia Activities of Daily Living Scale (LF-ADL), physician and patient ratings of improvement from baseline in dyskinesias on 7-point CGI-C and PGI-C scales, and responder analyses (subjects with >25% improvement from baseline) on UDysRS total score and LF-ADL, and % subjects with any improvement on PGI-C and CGI-C.

The safety population for all safety analyses consisted of all subjects who received at least 1 dose of nicotine or placebo. Efficacy analyses were conducted on all subjects who took at least 1 dose of study medication, had a baseline and at least one post-baseline assessment.

A total of 65 patients were randomized to treatment (nicotine=35, pbo=30) and a total of 63 patients completed the trial; medication compliance in each group was >90%. The patient population in this study was typical of those patients with LIDS. Overall, approximately 50% of patients in each group were Hoehn and Yahr Stage II, approximately 40% Stage III with the remainder Stage IV. Additionally, 90% of all patients were rated as having moderate disease or worse on the CGI-S, consistent with the baseline distribution of UPDRS motor scores. The baseline characteristics (mean+/−SD) are summarized below. There were no statistically significant differences in baseline parameters between the 2 groups.

Nicotine was generally safe and well-tolerated in PD patients with LIDS. Based on the mechanism of action of nicotine, no unexpected AEs occurred. Importantly, nicotine did not worsen, but improved UPDRS total scores.

A total of 11 subjects were withdrawn due to treatment-related AEs: 6 subjects in the nicotine group (1 subject each on 4 mg/day and 8 mg/day, and 2 subjects each in the 16 mg/day and 24 mg/day groups) and 5 subjects in the pbo group. The overall incidence of serious AEs (SAE) was low: 4 subjects in the nicotine group and 2 subjects in the pbo group, respectively. Importantly, all SAEs were assessed as unrelated to study medication. Overall, a higher percentage of subjects reported treatment-related AEs in the nicotine group (54%) compared to the pbo group (20%). The majority of adverse events were mild or moderate in intensity and transient in duration. The most common treatment-emergent AEs in the nicotine group (>5%) were nausea (31%), constipation and dizziness reported by 11% of subjects each, fatigue and non-specific pain reported by 9% of subjects each, and vomiting and nightmares reported by 6% subjects each. The respective incidences in the pbo group were: 3%, 3%, with the remainder 0%. Twenty-nine percent and 3% of subjects used rescue medication in the nicotine and pbo groups, respectively. Mean changes from baseline in blood chemistry, hematology, and vital signs were similar across treatment groups at all study visits. There were no clinically relevant changes in ECG parameters in either group. Serum cotinine levels increased with increasing dose as expected in patients treated with nicotine.

There were no differences in occurrences of impulsivity disorders, as assessed by a positive score on any JayMidi module; reported in 1 subject in each treatment group. Withdrawal symptoms, as assessed by the MNWS-R which has a maximal score of 60, were not a clinically relevant issue. At Week 10 (end of drug treatment) the scores in the nicotine and pbo groups were 7.5 and 6.7, respectively and decreased to 5.4 in the nicotine and 5.2 in the pbo group at end of the follow-up period.

Multiple instruments were used in an exploratory manner to assess the efficacy of nicotine on LIDS. There was a trend or statistically significant improvement in the nicotine group compared to pbo on the majority of patient- and physician-rated outcome measures.

Nicotine resulted in numerical improvement in the UPDRS in the mean change from baseline to Week 10 compared to placebo at every visit during drug treatment. The nicotine group also had a greater mean improvement in the UPDRS Part III score: maximum mean improvement was 2.0 points at Week 10 compared to a mean worsening of −0.4 points in the pbo group (FIG. 1). Importantly, the degree of absolute change from baseline in the nicotine group neared the change that has been considered the minimally clinically relevant change, despite the fact that the drug-treatment period was only 10 weeks in duration and the study was not powered as an efficacy study.

Figure 2:
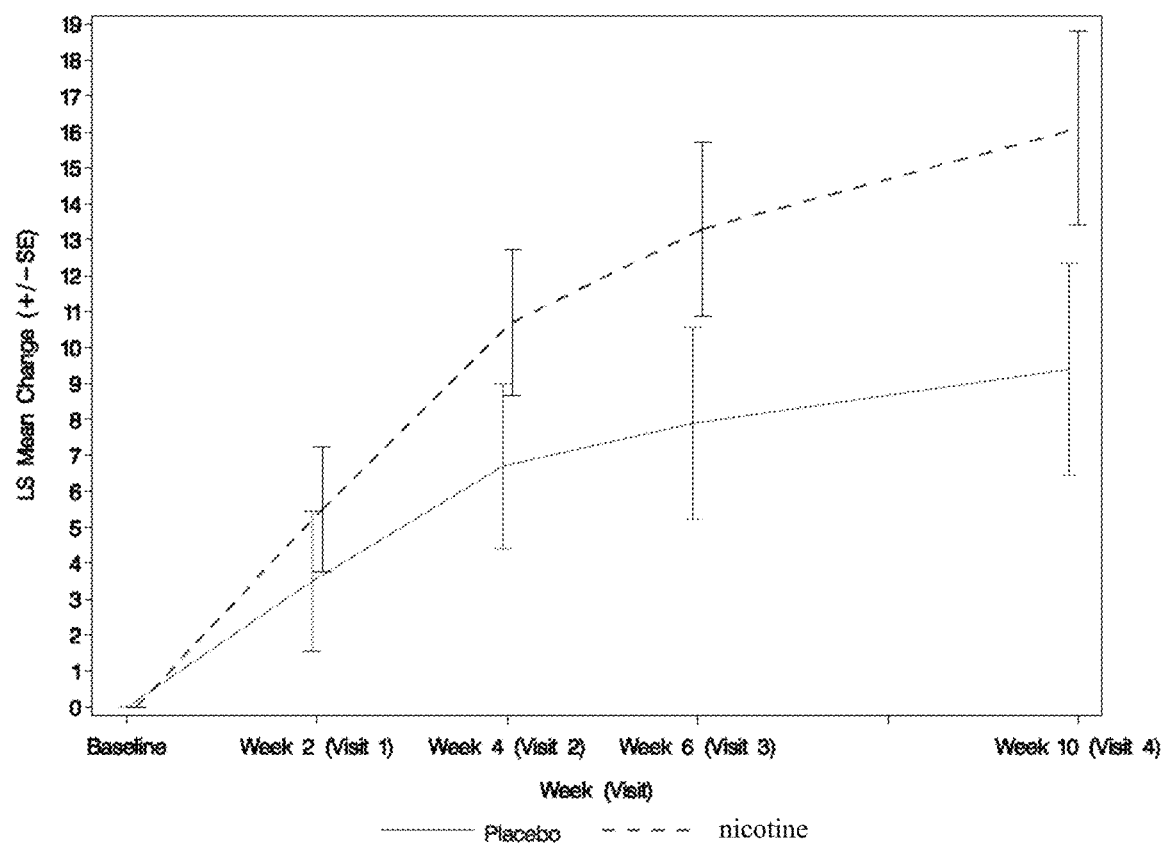
FIG. 2 illustrates mean change from baseline in Unified Dyskiensia Rating Scale Total Score for nicotine compared to placebo.
Figure 3:
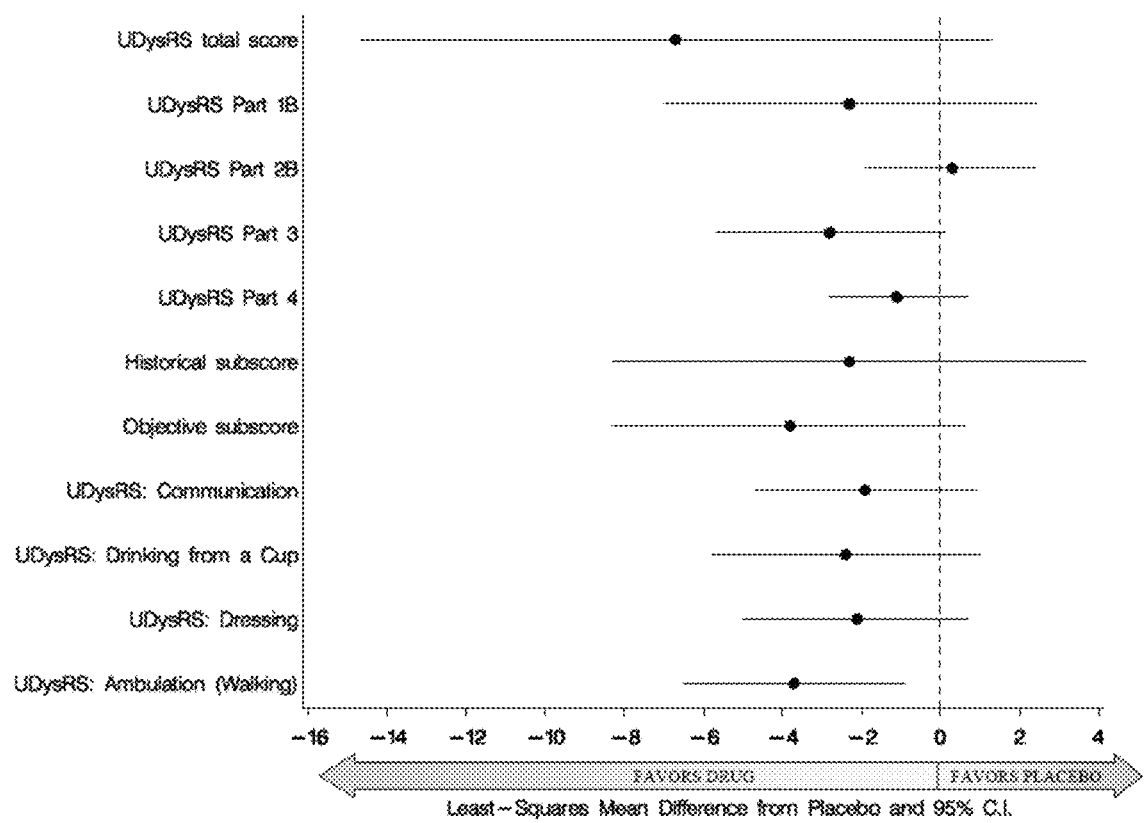
FIG. 3 depicts a forest plot of the Mean Difference between Placebo and nicotine in the change from Baseline to Week 10 of treatment.

Similar trends favoring nicotine were also observed on the UDysRS total score as illustrated in FIG. 2. Mean improvement from baseline and greater separation from pbo was observed at every study visit during the drug-treatment period. At Week 10, nicotine resulted in improvement on 9 of 10 subscores of the UDysRS as assessed by the mean changes from baseline compared to pbo, as shown in FIG. 3. Statistically significant improvement in ambulation occurred in those patients treated with nicotine versus pbo (p=0.01).

Figure 4:
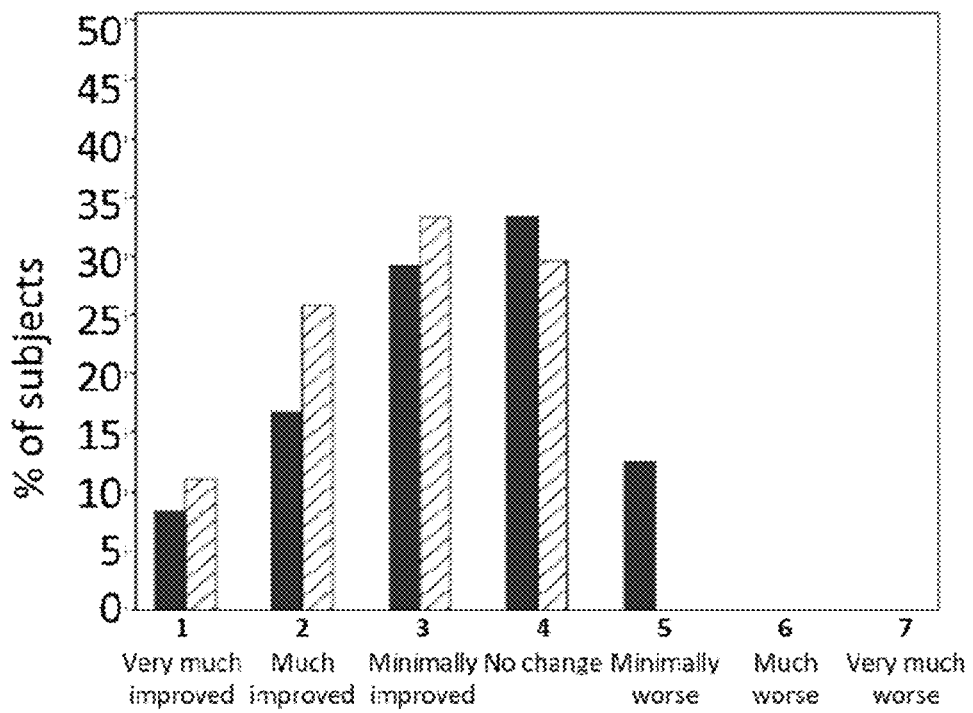
FIG. 4 shows percentage of subjects in each of CGI-C (upper panel) and PGI-C (lower panel) Categories after 10 weeks of treatment.
Figure 4:
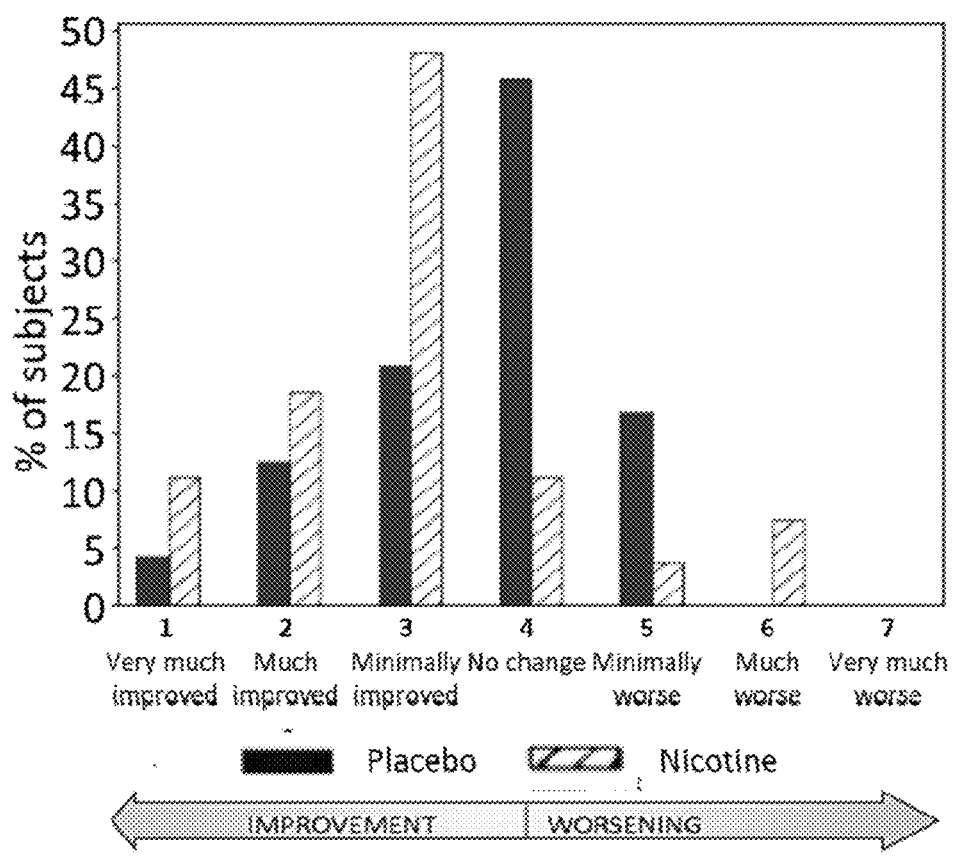

Other statistically significant differences favoring nicotine compared to pbo were observed on the LF-ADL responders and PGI-C responders. At Week 10, 56% of nicotine-treated subjects were responders on the LF-ADL compared to 25% in the pbo group (p=0.04). 78% of patients treated with nicotine rated themselves as having any degree of improvement compared to 38% of pbo-treated subjects (p=0.004, illustrated in FIG. 4). The distribution of nicotine subjects in each category, compared to pbo, was also significant (p=0.02). A similar, but not statistically significant pattern was also seen on the CGI-C.

Example 2: Formulation

Tablets are manufactured using a dry blend process, and hand made on a Carver 'Auto C' Press (Fred Carver, Inc., Indiana). The dry blend process consists of blending all of the ingredients in a plastic bag, and compressing into a 500 mg tablet (10 mg nicotine dose) using a 0.7086".times.0.3937" Mod Oval die (Natoli Engineering).

Tablets include nicotine, PEO Coagulant, Methocel K100M, and magnesium stearate. (PEO Coagulant=poly (ethylene oxide), grade PolyOx Coagulant, NF FP grade, manufactured by Union Carbide/Dow Chemical Company; Methocel K100M=hydroxypropylmethylcellulose, grade Methocel K100M, premium, manufactured by Dow Chemical Company; magnesium stearate, NF, supplied by Spectrum Chemical Company). Amounts of PEO Coagulant range from 10 to 90% by weight, amounts of Methocel K100M range from 10 to 90% by weight, and amounts of magnesium stearate range from 0 to 2% by weight.

The dissolution is determined in USP apparatus I (40 mesh baskets), 100 rpm, in deionized water. Samples, 5 ml at each time-point, are taken without media replacement at 1, 4 and 8 hours.

Example 3: Formulation

Example 2 is repeated with the percentage by weight of inactives as (i) 50% PEO Coagulant, 49% Methocel K100M, and 1% magnesium stearate; (ii) 89% PEO Coagulant, 10% Methocel K100M, and 1% magnesium stearate; and (iii) 10% PEO Coagulant, 89% Methocel K100M, and 1% magnesium stearate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pulsatile release dosage form for twice-daily administration, said form comprising a tablet comprising an effective amount of nicotine for treatment of symptoms of Parkinson's Disease or symptoms associated with dopaminergic treatment of Parkinson's Disease, wherein said tablet exhibits pulsatile release of said nicotine when administered, said pulsatile release comprising a first and second release peak, wherein said first release peak occurs within about two hours of administration, and said second release peak occurs between about two and about twelve hours of administration, and wherein about 1-2 mg of nicotine is released in the first release and about 2-3 mg of nicotine is released in the second release.

2. The dosage form according to claim 1, wherein said dosage form further comprises levodopa, carbidopa, or a combination thereof.

3. The dosage form according to claim 1, wherein said tablet comprises a coating and a core, wherein said coating comprises nicotine for the first release peak, and said core comprises nicotine for the second release peak.

4. The dosage form according to claim 3, wherein said coating is selected from an enteric coating, an erodible-matrix coating, a wax coating, an ethylcellulose coating, a silicone elastomer coating, and combinations thereof.

5. The dosage form according to claim 1, wherein said dosage form is capable of being administered so that one or more metabolites of said nicotine achieves a plasma level of about 1 to about 500 ng/ml within four hours of administration.

6. A delayed release dosage form for twice-daily administration, said form comprising a liquid filled capsule comprising an effective amount of nicotine for treatment of symptoms of Parkinson's Disease or symptoms associated with dopaminergic treatment of Parkinson's Disease, wherein said capsule comprises a hard gelatin outer surface, and wherein about 1-2 mg nicotine is released in a first release, and about 2-3 mg nicotine is released in a second release.

7. The dosage form according to claim 6, wherein nicotine is present at less than about 10 mg.

8. The dosage form of claim 6, wherein said dosage form is capable of being administered so that one or more metabolites of said nicotine achieves a plasma level of about 1 to about 500 ng/ml within four hours of administration.

9. The dosage form according to claim 6, wherein said dosage form further comprises levodopa, carbidopa, or a combination thereof.

10. An extended release dosage form for once-daily administration, said form comprising a capsule comprising an effective amount of nicotine for treatment of symptoms of Parkinson's Disease or symptoms associated with dopaminergic treatment of Parkinson's Disease, wherein said capsule comprises a powder comprising nicotine for providing a first release peak and a bead comprising nicotine for providing second release peak, and wherein said capsule achieves an efficacious plasma concentration of nicotine or a metabolite thereof within one hour from administration for a duration of at least six hours and further wherein said capsule achieves a peak plasma concentration of nicotine or a metabolite thereof at least about two hours after administration.

11. The dosage form according to claim 10, wherein said capsule comprises a water-swellable polymeric matrix.

12. The dosage form according to claim 10, wherein said capsule comprises a matrix comprising at least one swellable hydrophilic polymer that swells with water to increase its size to promote gastric retention of the dosage form in the stomach.

13. The dosage form according to claim 10, wherein nicotine is present at less than about 10 mg.

14. The dosage form of claim 10, wherein said dosage form is capable of being administered so that one or more metabolites of said nicotine achieves a plasma level of about 1 to about 500 ng/ml within one hour of administration.

15. The dosage form according to claim 10, wherein said dosage form further comprises levodopa, carbidopa, or a combination thereof.

16. A method of treating gait and balance problems in a subject, comprising administering an oral composition comprising nicotine, wherein the gait and balance problems are direct symptoms of Parkinson's Disease, and wherein about 1-2 mg of nicotine is released in a first release and about 2-3 mg of nicotine is released in a second release, and wherein nicotine or one or more metabolites of nicotine achieves an efficacious plasma level within about one hour of administration and further achieves a maximum plasma level peak from two to twelve hours from administration.

17. The method of claim 16, wherein the nicotine is administered in a dose of less than about 10 mg.

18. The method of claim 16, wherein said oral composition is capable of being administered so that nicotine or one or more metabolites of nicotine achieves a plasma level of about 1 to about 500 ng/ml within four hours of administration.

* * * * *